United States Patent [19]
Kurtz et al.

[11] 4,434,659
[45] Mar. 6, 1984

[54] TWO-DIMENSIONAL SCANNER APPARATUS

[75] Inventors: George W. Kurtz; Ben F. Bankston, both of Huntsville, Ala.

[73] Assignee: The United States of America as represented by the Administrator of the National Aeronautics and Space Administration, Washington, D.C.

[21] Appl. No.: 350,474

[22] Filed: Feb. 19, 1982

[51] Int. Cl.³ .............................................. G01N 29/04
[52] U.S. Cl. ........................................ 73/620; 73/633; 324/262; 74/58
[58] Field of Search .......................... 73/620, 629, 633; 324/261, 262; 74/58, 128

[56] References Cited

U.S. PATENT DOCUMENTS

| | | | |
|---|---|---|---|
| 2,182,522 | 12/1939 | Lindsey | 74/58 |
| 3,501,968 | 3/1970 | Fredell | 74/128 |
| 3,898,838 | 8/1975 | Connelly | 73/634 |
| 4,170,145 | 10/1979 | Kennedy et al. | 73/620 |
| 4,294,118 | 10/1981 | Shiraiwa et al. | 73/620 |
| 4,304,133 | 12/1981 | Feamster | 73/633 |

Primary Examiner—Gerald Goldberg
Assistant Examiner—John E. Chapman, Jr.
Attorney, Agent, or Firm—Joseph H. Beumer; John R. Manning; Leon D. Wofford, Jr.

[57] ABSTRACT

An X-Y scanner is illustrated which utilizes an eddy current or ultrasonic current test probe for detecting surface defects in small flat plates and the like. The apparatus includes a scanner C which travels on a pair of slide tubes (20) in the X-direction. The scanner is, in turn, carried on a carriage B which slides in the Y-direction. The scanner C is driven in the X-direction by means of a helix shaft (44) having a closed-loop helix groove (46) in which a follower pin 38 carried by scanner C rides. The carriage B is moved incrementally in the Y-direction upon the completion of travel of the scanner back and forth in the X-direction by means of an indexing means E which includes an indexing actuator (54) and an indexing gear (50). Actuator (54) is in the form of a ratchet which engages ratchet gear (52) upon return of the scanner to the indexing position whereupon the indexing gear (50) is rotated a predetermined increment along a rack gear (48) to move carriage B incrementally in the Y-direction. Thus, simplified highly responsive mechanical motion may be had in a small lightweight portable unit for accurate scanning of small areas.

6 Claims, 3 Drawing Figures

U.S. Patent    Mar. 6, 1984    4,434,659
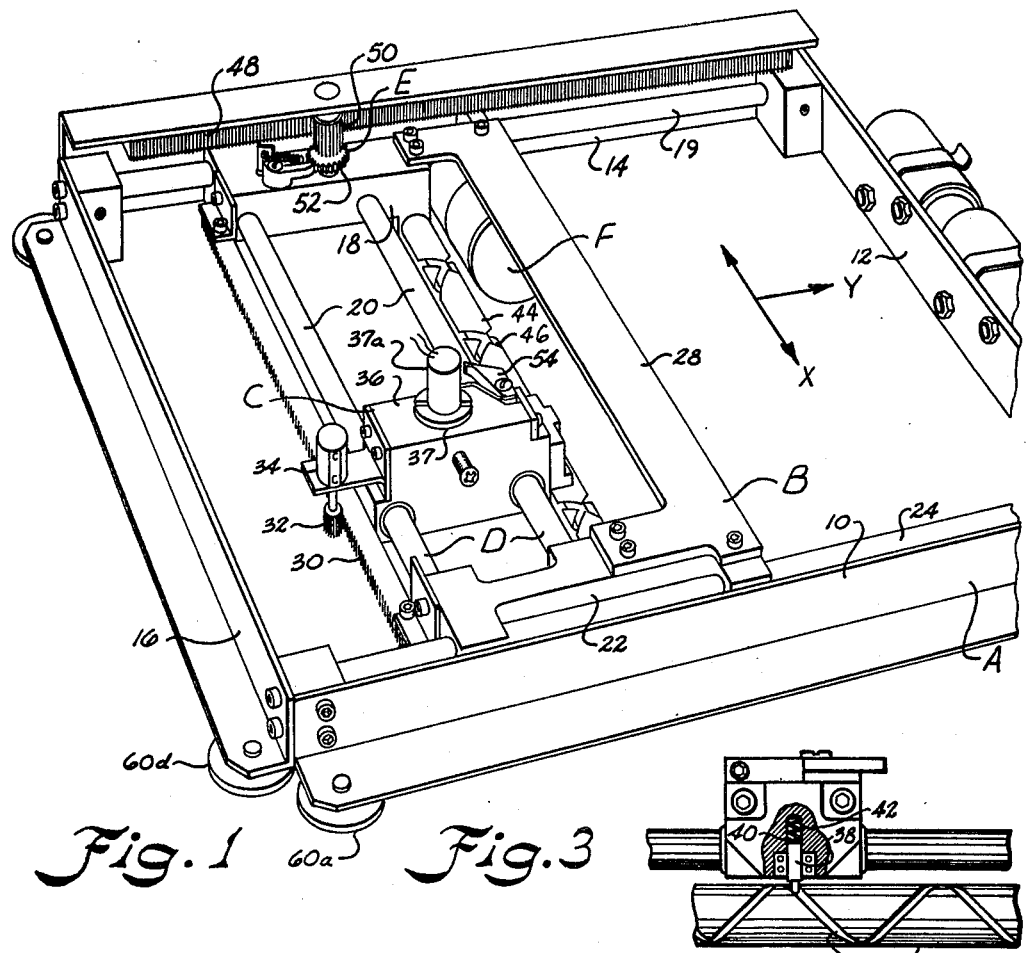
Fig. 1
Fig. 3
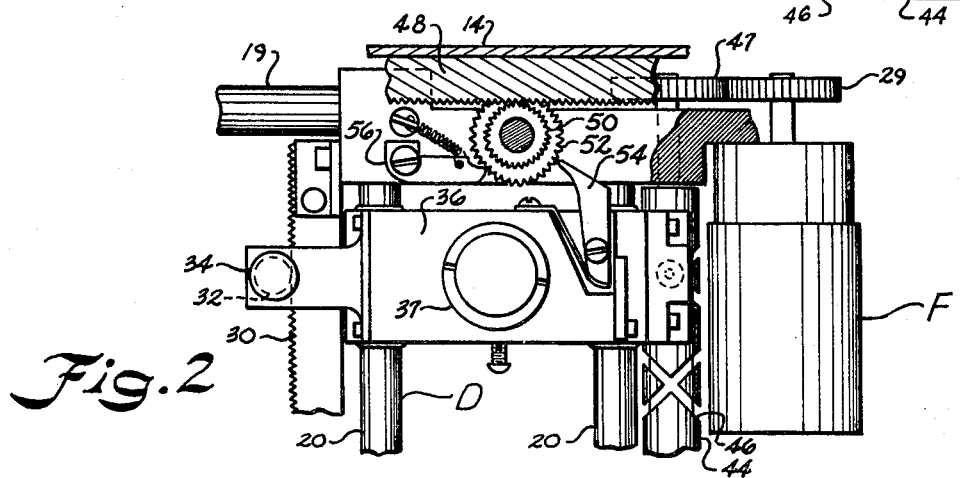
Fig. 2

TWO-DIMENSIONAL SCANNER APPARATUS

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The invention relates to the testing of small flat plate areas for surface defects by utilizing eddy current or ultrasonic test probes. Heretofore, electromechanical scanners have been utilized such as shown in U.S. Pat. Nos. 3,038,329 and 3,898,838.

Typically, prior electromechanical scanners available on the market have been large, heavy constructions which are not readily portable and have utilized plural motor drives for the X and Y scan directions. The scanners are not readily portable and cannot effectively scan areas on small scales in a reliable manner with the degree of accuracy required to detect flaws in raw material utilized in critical applications in space structures and hardware.

Accordingly, an important object of the present invention is to provide a portable reliable mechanized scanner for testing small flat plate areas for surface defects by utilizing eddy current or ultrasonic test probes.

Yet another important object of the present invention is to provide an X-Y scanner for material testing which is efficient and highly accurate by utilizing simple and reliable mechanical drive movements in the X and Y directions.

Yet another important object of the present invention is to provide an electromechanical X-Y scanner which employs simple direct drive means eliminating the need for belts and a plurality of drive motors.

SUMMARY OF THE INVENTION

According to the present invention the above objectives are accomplished by providing a lightweight frame on which a carriage is slidably carried in the Y direction. Upon the carriage is slidably carried a scanner support member which bridges and slides upon two slide tubes. The scanner support carries on eddy current detector and a follower pin which engages the helix of a closed-loop helix shaft rotated by a miniature motor. As the helix shaft rotates the support travels in the X-direction along the shaft and when the follower pin reaches the end of the helix travel, the scanner support is reversed in its direction. An index actuator on the scanner support actuates a cam gear when the scanner support reaches the end of its travel in the reverse direction. The cam gear is mounted on the carriage and engages a gear rack carried on the frame such that the cam gear indexes the carriage travel in the Y-direction in a predetermined increment of movement. In this manner, a highly efficient and portable scanner apparatus is provided which is highly responsive and effective for accurately detecting surface defects in small areas of flat plate materials.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 1 is a perspective view illustrating apparatus for scanning small area flat stock surfaces according to the invention, FIG. 2 is a plan view illustrating mechanical indexing movement of a scanner according to the invention, and FIG. 3 is an elevation of the apparatus of FIG. 1 as viewed from the side which travels in the X-direction during scanning.

DESCRIPTION OF A PREFERRED EMBODIMENT

The drawings illustrate a two-dimensional scanner apparatus for accurately scanning small surface areas of flat materials and the like for surface defects by utilizing eddy currents or ultrasonic test probes. As illustrated, the apparatus includes a frame A and carriage means B slidably carried by the frame for movement in a first or Y-direction. Scanner means C is carried by the carriage means and is adapted for carrying the test probe which detects a condition on the surface which it scans. Support means D supports the scanner means on carriage means B for movement in a second or X-direction. Index means E moves the carriage B in the Y-direction in response to a complete movement of the scanner means in the X-direction. Drive means F is provided for moving the scanner means in the X-direction.

Referring now in more detail to the drawings, the frame A is illustrated as including a rectangular frame having four sides 10, 12, 14 and 16 cut from a lightweight aluminum stock and joined integrally together. Carriage means B includes a main slide support 18 which slides in the Y-direction on a slide rod 19, and supports one end of a pair of slide tubes 20. A second carriage slide support 22 is located at the other end of carriage B which supports the opposing ends of the slide tubes 20. Secondary slide support 22 slides over Y-direction slide rod 24. Slide rods 24 and 19 are carried on frame sides 10 and 14, respectively, by any suitable means such as being journaled in support blocks affixed in corners of the frame A as illustrated. A flange support 28 extends between the slide supports 18 and 22 by means of which the drive motor F is carried and affixed to the carriage.

A gear rack 30 is carried between the slide supports 18 and 22 which engages a gear 32 of a potentiometer 34 carried by the scanner means C. Potentiometer 34 feeds back the X-position to an oscilloscope and recording means (not shown). A similar potentiometer (not shown) is carried by slide support 22 and engages a gear rack (not shown) carried by frame A for recording the Y-position.

Scanner means C includes a scanner support 36 which slides over the slide tubes 20 and carries the detector probe, illustrated schematically at 37a, inserted in clamping ring 37 which may be adapted to hold any conventional eddy current or ultrasonic current probe of small diameter ranging from one-half to three-quarters of an inch. Smaller diameter probes may also be utilized. The frequency and power required for the eddy current operation may be determined in accordance with conventional techniques providing flaw detecting capabilities as desired. The scanner support 36 carries a follower pin 38 by means of a recess or bore 40 in which the pin is slidably carried and biased downwardly by spring 42.

Drive means for moving the scanner support and detector 37a in the X-direction further includes a shaft 44 having its ends rotatably journalled in the slide supports 18 and 22. Shaft 44 includes a closed loop helix groove 46 formed in the surface thereof in which follower pin 38 rides. The helix groove is machined in the shaft to a pitch of 1⅛ inches so that full spirals are created with closed loop radius at both ends. As the shaft continuously rotates the follower pin 38 rides in the helix groove causing the scanner support member 36 to traverse back and forth in the X-direction. When the follower pin comes to the end of the helix groove, the direction of the follower and scanner support is automatically reversed whereupon the detector probe traverses the surface in the reverse direction for one complete movement of scanner C support. Motor F includes a gear 29 carried on its output shaft which engages gear 47 on helix shaft 44. The helix groove and shaft speed (45 rpm) are preferably designed to drive scanner support 36 about three inches per second.

Index means E includes a gear rack 48 carried on the side frame 14 and indexing gear means which includes a cam gear 50 rotatably carried on slide support 18 of carriage B engaging the gear rack and a ratchet gear 52. Gear 52 is carried coaxially and affixed for rotation with the cam gear 50 and is engaged by an indexing ratchet actuator 54 affixed to the scanner support 36 such that when the scanner support reaches its extreme most indexing position ratchet 54 actuates the ratchet gear 52 indexing it one increment to rotate the index gear 50 a corresponding increment. The entire carriage B is then indexed and moved incrementally in the Y-direction by drive along the rack gear 48. The indexing means is completed by means of a pawl 56 also carried on the main slide support 18 which engages the ratchet gear 52 in a conventional ratchet pawl operation to limit and control the incremental movement of the ratchet and cam gears. Indexing of one-sixteenth of an inch is preferred for each complete movement of scanner C in the Y-direction.

In operation, the scanner apparatus is first checked for levelness prior to operation and adjusted to a level condition by means of adjusting the four vertically adjustable legs 60a, 60b, 60c and 60d. The scanner is then positioned over the plate or surface to be scanned. The eddy current probe 37a is then put in its normal position in clamp 37 of scanner means C and the distance of the probe face to the surface is checked. The scanner support 36 is moved to the extreme Y index position opposite the drive motor F of the frame. The index pawl is disengaged from the index gear 52 during this initial movement. The pawl is held away from the index gear and the assembly is moved to its start position. The scanner support 36 is then moved to its approximate mid scan position on the support tubes by either turning the helix shaft 44 or the gear coupling the helix shaft to the output shaft of the motor. The supply for the eddy current equipment is then turned on and the power to the scanner is likewise turned on and the scanning operation commences.

Movement in the X-direction is preferably accomplished over a travel of eight inches in approximately three seconds, while Y index of approximately 1/16" is accomplished every two scans in the X direction. Travel in the Y direction is approximately eight inches. Combined X-Y scanning enables a coverage of sixty-four square inches. Indexing is only in one direction of Y travel. The cam gear 50 must be disengaged at the end of the Y travel and the scanner and its support mechanism returned to the start position of Y index.

Thus, it can be seen that a highly effective mechanical drive movement for a small-scale two-dimensional scanner can be had where plural motors and belt drives are eliminated and accurate scanning of small areas can be had.

While a preferred embodiment of the invention has been described using specific terms, such description is for illustrative purposes only, and it is to be understood that changes and variations may be made without departing from the spirit or scope of the following claims.

What is claimed is:

1. A two-dimensional scanner apparatus for scanning a surface in two-dimensions consisting of an X-direction and a Y-direction, said apparatus comprising:

a frame;

a carriage means slidably carried by said frame for movement in said Y-direction;

scanner means carried by said carriage means adapted for carrying a detector probe for detecting a condition on said surface;

support means supporting said scanner means on said carriage means for movement of said scanner means in said X-direction;

drive means for moving said scanner means across said surface in said X-direction;

mechanical indexing means for indexing and incrementally moving said carriage means in said Y-direction in a predetermined increment in response to a complete movement of said scanner means in said X-direction;

said drive means including a shaft rotatably carried by said carriage means having a closed-loop helix groove formed therein;

follower means engaging within said groove causing said scanner means to travel along said shaft as said shaft rotates and reverses said direction of travel when said follower means reaches the end of said helix;

a drive motor operatively connected for rotating said shaft; and an actuating means carried by said scanner means which mechanically engages said mechanical indexing means and actuates said mechanical indexing means upon said scanner means traveling said complete movement in said X-direction for indexing said indexing means and thereby effecting said predetermined increment in said Y-direction.

2. The apparatus of claim 1 wherein said indexing means includes:

a gear rack carried by said frame;

indexing gear means carried by said carriage means meshing with said gear rack; and said actuating means engaging said indexing gear means when said scanner means reaches the end of its travel in said X-direction during said complete movement, effecting incremental rotation of said indexing gear means and thereby effecting said predetermined increment in said Y-direction.

3. The apparatus of claim 2 wherein said indexing gear means includes a cam gear meshing with said gear rack and a ratchet gear engaged by said actuating means for rotating said cam gear in said incremental rotation.

4. The apparatus of claim 3 wherein said actuating means includes an indexing ratchet carried by said scanner means.

5. The apparatus of claim 1 wherein said complete movement of said scanner means includes travel of said scanner means back and forth across said surface one time.

6. A two-dimensional scanner apparatus for scanning a surface in two-dimensions consisting of an X-direction and a Y-direction, said apparatus comprising:
   a frame;
   a carriage means slidably carried by said frame for movement in said Y-direction;
   scanner means carried by said carriage means for movement in said X-direction adapted for carrying a detector probe for detecting a condition on said surface;
   support means supporting said scanner means on said carriage means for movement of said scanner means in said X-direction;
   indexing means incrementally moving said carriage means in said Y-direction in a predetermined increment in response to a complete movement of said scanner means in said X-direction;
   a shaft rotatably carried by said carriage means having a closed-loop helix groove formed therein;
   following means carried by said scanner means engaging within said groove causing said scanner means to travel along said shaft as said shaft rotates and reverses said direction of travel when said follower means reaches the end of said helix;
   a drive motor operatively connected for rotating said shaft;
   frame gear rack means carried by said frame; and
   said indexing means including an indexing gear meshing with said frame gear rack means and actuating means engaging said indexing gear when said scanner means reaches the end of its travel in said X-direction during said complete movement, effecting incremental rotation of said indexing gear and thereby effecting said predetermined increment in said Y-direction.

* * * * *